United States Patent
Varghese et al.

(10) Patent No.: US 9,884,202 B2
(45) Date of Patent: Feb. 6, 2018

(54) DEVICE FOR LIGHT BASED SKIN TREATMENT

(71) Applicant: KONINKLIJKE PHILIPS N.V., Eindhoven (NL)

(72) Inventors: Babu Varghese, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 155 days.

(21) Appl. No.: 14/381,329

(22) PCT Filed: Feb. 27, 2013

(86) PCT No.: PCT/IB2013/051560
§ 371 (c)(1),
(2) Date: Aug. 27, 2014

(87) PCT Pub. No.: WO2013/128380
PCT Pub. Date: Sep. 6, 2013

(65) Prior Publication Data
US 2015/0032191 A1    Jan. 29, 2015

Related U.S. Application Data

(60) Provisional application No. 61/604,021, filed on Feb. 28, 2012.

(51) Int. Cl.
*A61N 5/06* (2006.01)
*A61B 18/20* (2006.01)
*A61B 18/00* (2006.01)

(52) U.S. Cl.
CPC .......... *A61N 5/0616* (2013.01); *A61B 18/203* (2013.01); *A61B 2018/00452* (2013.01);
(Continued)

(58) Field of Classification Search
CPC .......... A61N 5/0616; A61N 2018/2035; A61B 18/203
(Continued)

(56) References Cited

U.S. PATENT DOCUMENTS 5,400,420 A * 3/1995 Boehme ............... G02B 6/3803
                                                          385/15
6,682,524 B1    1/2004 Elbrecht
(Continued)

FOREIGN PATENT DOCUMENTS

DE         19832221 A1    2/2000
JP      2012034828 A  *   2/2012
(Continued)

OTHER PUBLICATIONS

JP 2012034828 A, Maruo, Katsuhiko, espacenet English Translation.*
(Continued)

*Primary Examiner* — Christopher A Flory
*Assistant Examiner* — Jonathan Kuo

(57) ABSTRACT

A device (10) for light based skin treatment is provided. The device (10) comprises a light source (18) for providing an incident light beam (21) for treating a skin (30), optical elements for focusing the incident light beam (21) in a focal point (22) inside the skin (30), and a skin interface element (11) for, during use of the device (10), providing optical coupling of the incident light beam (21) from the device (10) into the skin (30). The skin interface element (11) comprises a transparent exit window (12) for allowing the incident light beam (21) to leave the device (10), on top of the exit window (12), a transparent mixture (13) of a polar substance and an apolar substance, and on top of the transparent mixture (13), a transparent foil (14), the transparent foil (14) being more hydrophobic than the exit window (12).

6 Claims, 1 Drawing Sheet

(52) U.S. Cl.
CPC ............... *A61B 2018/2035* (2013.01); *A61N 2005/0643* (2013.01)

(58) Field of Classification Search
USPC ...... 607/80, 88–95; 601/15, 17; 606/2, 9–19
See application file for complete search history.

(56) References Cited

U.S. PATENT DOCUMENTS

| | | |
|---|---|---|
| 2007/0043342 A1 | 4/2007 | Kleinberger |
| 2010/0087739 A1 | 4/2010 | Lucassen |
| 2010/0324544 A1 | 12/2010 | Fertner |
| 2012/0029417 A1* | 2/2012 | Samain ............ A61K 8/49 604/20 |
| 2013/0073001 A1* | 3/2013 | Campbell ......... A61N 1/0476 607/50 |
| 2014/0074010 A1* | 3/2014 | Veres .............. A61N 5/06 604/20 |

FOREIGN PATENT DOCUMENTS

| | | |
|---|---|---|
| WO | 0133278 A1 | 5/2001 |
| WO | 02091394 A1 | 11/2001 |
| WO | 2008001284 A2 | 1/2008 |
| WO | 2008001584 A1 | 1/2008 |
| WO | 2010031777 A2 | 3/2010 |

OTHER PUBLICATIONS

M.R Alexiades Armenakas, J.S Dover, K.A Arndt, "The spectrum of laser skin resurfacing: Nonablative, fractional, and ablative laser resurfacing", American Academy of Dermatology, (2008).

L. Habbema, R. Verhagen, R. Van Hal, Y. Liu, B. Varghese, "Minimally invasive non-thermal laser technology using laser-induced optical breakdown for skin rejuvenation", Journal of Biophotonics, (2011).

* cited by examiner

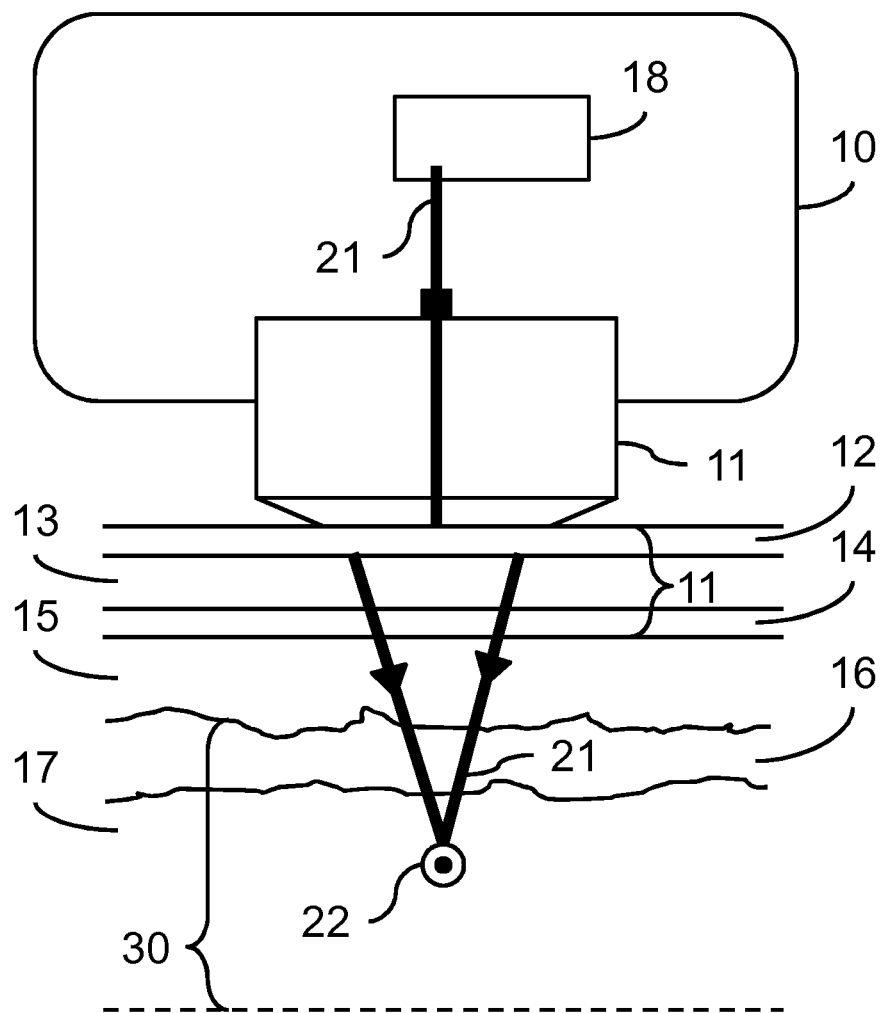

DEVICE FOR LIGHT BASED SKIN TREATMENT

This application is the U.S. National Phase application under 35 U.S.C. § 371 of International Application No. PCT/IB2013/051560, filed on Feb. 27, 2013, which claims the benefit of U.S. Provisional Application No. 61/604,021 filed on Feb. 28, 2012. These applications are hereby incorporated by reference herein.

FIELD OF THE INVENTION

This invention relates to a device for light based skin treatment, the device comprising a light source for providing an incident light beam for treating a skin, optical elements for focusing the incident light beam in a focal point inside the skin, and a skin interface element for, during use of the device, providing optical coupling of the incident light beam from the device into the skin, the skin interface element comprising a transparent exit window for allowing the incident light beam to leave the device.

This invention further relates to a system for light based skin treatment, to a coupling foil and a method for providing optical coupling of an incident light beam from a device for light based skin treatment into a skin.

BACKGROUND OF THE INVENTION

Such a skin treatment device is, e.g., known from the published international patent application WO 2008/001284 A2. Said application discloses a skin treatment device with a laser source and focusing optics. The device comprises a housing with an exit window through which a laser beam is emitted. The exit window may be made of a transparent material or may simply be an aperture in the housing. The device creates a focal spot in a dermis layer of the skin to be treated. The power of the laser beam and the dimensions of the focal spot are selected such that laser induced optical breakdown (LIOB) is induced in the focal spot in the skin in order to stimulate re-growth of skin tissue and to reduce wrinkles.

The focal spot is created at a fixed treatment depth, somewhere between 0.2 and 2.0 mm. This depth is selected based on the typical composition of human skin. In some cases, however, the optimal treatment depth may be different. The optimal treatment depth depends on, e.g., the thickness of the stratum corneum and the epidermis. To prevent a lens effect by the skin and by the curvature of the wrinkle, an index-matching material may be applied to the skin in order to fill the wrinkle between the epidermis and the exit window. The index-matching material should have an index of refraction approximately between the index of refraction of the exit window and that of the epidermis, preferably approximately equal to the refractive index of the epidermis. In the ideal case, the exit window and the index-matching material have the same index of refraction as the epidermis, i.e. roughly 1.4.

However, the mere addition of an index-matching material in order to prevent a mismatch in the refractive index is not sufficient for obtaining the desired control over the light intensity in the focal spot and over the exact position of the focal spot in the skin. The skin surface (stratum corneum) shows microscopic fluctuations in roughness due to vertically stacked corneocytes. The coupling of light through the optically rough stratum corneum, which resembles an array of micro lenses, is difficult and results in loosely focused light beams. This causes a decrease of the ratio of the photon density in the focal spot to the background and a less efficient LIOB creation in the focus.

OBJECT OF THE INVENTION

It is an object of the invention to improve the coupling of the light into the skin and the efficiency of the LIOB creation in the dermis.

SUMMARY OF THE INVENTION

According to a first aspect of the invention, this object is achieved by providing a device for light based skin treatment, the device comprising a light source, optical elements and a skin interface element. The light source provides an incident light beam for treating a skin. The optical elements are provided for focusing the incident light beam in a focal point inside the skin. The skin interface element, during use of the device, provides optical coupling of the incident light beam from the device into the skin. The skin interface element comprises a transparent exit window for allowing the incident light beam to leave the device. On top of the exit window, a transparent mixture of a polar substance and an apolar substance is provided. A transparent foil is provided on top of the transparent mixture. The transparent foil is more hydrophobic than the transparent exit window.

With such a skin interface element comprising different layers with different physical, optical and chemical properties, the coupling of the light into the skin is significantly improved. Like in the already known optical skin treatment device, the surface of the exit window flattens the skin. This mechanical flattening is, however, not sufficient for obtaining the desired efficient LIOB creation. From, e.g., the international patent application WO 2010/031777 it is known to use a gel for reducing a mismatch between the refractive indexes of the skin and the exit window. Such a gel, however, does also not overcome the optical coupling problems associated with the rough surface of the stratum corneum.

The inventors have obtained better results using massage oils or other types of organic oils. The strong capillary effect of the oil improves the optical coupling between the interface element and the top layers of the skin. It is to be noted that this capillary effect can also be provided by other fluids having a suitable viscosity of about 20 to about 80 mPa·s, preferably about 20 mPa·s. The capillary effect of the fluid overcomes the microstructure variations and enables the efficient optical coupling. The capillary effect is proportional to the surface tension of the fluid, radius of capillary etc. Furthermore, the action will be faster for low viscous fluids. Highly viscous fluids can also provide the desired capillary action, however at relatively slow speeds. This result in slight modification of the radius of capillary as the drop of fluid is pulled along the surface of skin, thereby enhancing the effect.

Also the contact angle that the drop of viscous fluid makes as it comes in contact with the skin affects the speed of the capillary action. Preferred contact angles between the fluid and the skin are in the range 0-45°, and smaller contact angles are preferred over larger angles.

According to the invention, this capillary effect is significantly enhanced by adding the transparent and relatively hydrophobic foil and the transparent mixture of a polar and an apolar substance between the skin and the transparent exit window. The transparent mixture provides for a smooth transition between the more hydrophilic transparent exit window, which is usually made of glass or a plastics material, and the foil, which results in a flat foil surface. The surface of the foil and the skin allow the applied oil to be effectively smeared throughout the microstructure variations of the stratum corneum, resulting in uniform optical coupling.

The transparent mixture is provided on top of the exit window and the foil is applied on top of the mixture. Regardless of the actual orientation of the device, 'on top' means that it is the next layer seen from the direction of the incident light beam coming from the light source.

For optimal optical coupling between the device and the skin, the transparent mixture should have a refractive index that lies between the refractive indexes of the foil and the transparent exit window.

According to a further aspect of the invention, a coupling foil is provided for optically coupling an incident light beam from a transparent exit window of a skin interface element of a device for light based skin treatment. The coupling foil is comprised of a transparent foil, the transparent foil at one side being provided with a transparent mixture of a polar substance and an apolar substance. Preferably, the foil is more hydrophobic than the transparent material from which the transparent exit window is made, which is typically plastics or glass. Such a coupling foil can be used together with the optical skin treatment devices that are already known from the prior art. The main requirement for the optical skin treatment device is that it has a suitable exit window, e.g. made of glass or plastics. The coupling foil may be a dispensable product which is applied to the device just before each skin treatment. For example, the coupling foil is a covering for pulling over at least the transparent exit window of the interface element of the device for light based skin treatment.

It is to be noted that the transparent foil and the transparent mixture may be provided separately. Before applying the covering to the interface element, the transparent mixture should then first be applied to the transparent exit window and/or the surface of the covering that is going to face the transparent exit window. In a similar way the viscous fluid, e.g. massage oil or another type of organic oil, to be applied between the skin and the transparent foil may already be present on the transparent foil surface or could be provided separately.

According to a further aspect of the invention, a system for light based skin treatment is provided, the system comprising a device for light based skin treatment and a coupling foil. The device comprises a light source for providing an incident light beam for treating a skin. The device further comprises optical elements for focusing the incident light beam in a focal point inside the skin. The device further comprises a skin interface element for, during use of the device, providing optical coupling of the incident light beam from the device into the skin, the skin interface element comprising a transparent exit window for allowing the incident light beam to leave the device. The coupling foil comprises a transparent foil, wherein the transparent foil, at one side, is provided with a transparent mixture of a polar substance and an apolar substance. The transparent foil is more hydrophobic than the transparent exit window of the device.

According to a further aspect of the invention, a method for optically coupling of an incident light beam from a device for light based skin treatment into a skin is provided, the method comprising applying a fluid having a viscosity of about 20 to about 80 mPa·s. to the skin, applying a transparent foil to the skin provided with the fluid, applying a transparent mixture of a polar substance and an apolar substance to a side of the transparent foil facing away from the skin, and pressing a transparent exit window of a skin interface element of the device to the transparent foil provided with the transparent mixture, the transparent foil being more hydrophobic than the transparent exit window.

These and other aspects of the invention are apparent from and will be elucidated with reference to the embodiments described hereinafter.

BRIEF DESCRIPTION OF THE DRAWINGS

In the drawings:
FIG. 1 schematically shows a skin treatment device according to the invention.

DETAILED DESCRIPTION OF THE INVENTION

FIG. 1 schematically shows a skin treatment device 10 according to the invention. The device 10 comprises a light source 18 for providing an incident light beam 21 for treating human or animal skin 30. The incident light beam 21 is typically a pulsed laser. For example, Nd:YAG lasers with emission at 1064 µm (micrometer) are used for laser induced optical breakdown (LIOB) skin treatment. Optical elements are provided for focusing the pulsed laser beam 21 inside the skin 30. Part or all of the optical elements may be provided in an interface element 11 which, during use of the device 10, is pressed onto or makes contact with the skin 30 to be treated.

The skin 30 comprises multiple layers with different optical properties. The epidermis 16 is composed of the outermost layers and forms a waterproof protective barrier. The outermost layer of the epidermis is the stratum corneum which, due to its microscopic fluctuations in roughness, impedes the coupling of light between the device 10 and the skin 30. Underneath the epidermis 16, the dermis 17 is situated. The dermis 17 comprises the collagen fibers at which the skin treatment is aimed. The purpose of the skin treatment is to create a focus 22 of the pulsed laser beam 21 in the collagen of the dermis 17 in order to create microscopic lesions which result in new collagen formation.

In the figure, part of the interface element 11 as well as part of the skin 30 is enlarged in order to clarify its most important aspects. The interface comprises a regular transparent exit window 12 which is typically made of a relatively hydrophilic material, such as glass or plastics. For optimum optical coupling, the refractive index of the material of the exit window 12 is preferably close to that of the epidermis. For human skin, the refractive index typically is around 1.4.

According to the invention, some additional layers 13, 14, 15 are provided in between the exit window 12 and the skin 30. Directly on the outer surface of the exit window 12, a transparent mixture 13 of a polar and an apolar substance is provided. The mixture 13 may be a gel or liquid which, due to its particular composition, adheres well to the exit window 12 above and the foil 14 underneath. This assures that the foil 14 will remain flat and the coupling of the light 21 into the skin 30 is optimal. As a suitable example, the mixture 13 may comprise polypropylene glycol (PPG) and polyethylene glycol (PEG). The transparent foil 14 may, e.g., be a thin polyethylene terephthalate (PET) foil. For optimal optical coupling between the device 10 and the skin 30, the transparent mixture 13 and the foil 14 should have refractive indexes that lie between the refractive indexes of the skin 30 and the exit window 12.

Before use of the device 10 some oil, preferably an organic oil, is applied to the skin 30 to be treated. For optimum results, the amount of oil 15 to be applied should be well controlled, for example in the order of 10-50 μl (microliters). The hydrophobic nature of the foil 14 and the epidermis layer 16 of the skin 30, allows the drop of oil to be effectively smeared throughout the microstructure variations of the skin 30 surface, resulting in uniform optical coupling. Instead of oil, other fluids with a suitable viscosity may be used.

The layers of the transparent mixture 13 and the foil 14 may be an integrated part of the interface element 11 of the skin treatment device 10. These layers 13, 14 and/or the complete interface element 11 may be substitutable. The oil 15 is typically provided separately, but may be provided from a refillable reservoir in the device 10.

The transparent foil 14 may be provided as a separate substitutable covering. Also the transparent mixture 13 may be provided separately. In that event, before each use of the device 10, the user applies some amount of the mixture 13 to the exit window 12 of the interface element 11 and covers it with a new covering. Of course, the mixture 13 and the covering may also be substituted after being used twice, 5 or 10 times. The covering may be provided with the mixture 13 already applied to its inner surface, which would make it unnecessary for the user to apply the mixture 13 to the exit window 12 before applying the covering. Optionally, the outer surface of the covering is already provided with the oil 15 and the oil 15 does not have to be provided separately.

Alternatively, the oil 15, the foil 14 and the mixture 13 are all provided separately and applied to the skin one by one before the exit window 12 of the interface element 11 of a skin treatment device 10 is pressed to the foil 14 covered with the mixture 13. Or oil 15 and foil 145 are applied to the skin 30 and the mixture is provided to the exit window 12.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A device for light based skin treatment, the device comprising:
   a light source for providing an incident light beam for treating a skin,
   optical elements for focusing the incident light beam in a focal point inside the skin,
   a skin interface element adapted to provide optical coupling of the incident light beam from the device into the skin, the skin interface element comprising a transparent exit window adapted to allow the incident light beam to leave the device, and
   a transparent foil being provided as a separate replaceable covering arranged and configured to be pulled over at least the transparent exit window, an inner surface of the covering including an application of a transparent mixture of a polar substance and an apolar substance and an outer surface of the covering including an application of an organic oil.

2. A device for light based skin treatment according to claim 1, wherein the transparent exit window is made of glass or plastics.

3. A device for light based skin treatment according to claim 1, wherein the light source and the optical elements are arranged for providing the incident light beam to induce optical breakdown of skin cells.

4. A device for light based skin treatment according to claim 1, wherein the transparent foil is more hydrophobic than a material from which the transparent exit window is made.

5. A device for light based skin treatment according to claim 1, wherein the transparent mixture has a refractive index which lies in between a refractive index of the transparent foil and a refractive index of the transparent exit window.

6. A device for light based skin treatment according to claim 1, wherein the transparent foil comprises polyethylene terephthalate (PET).

* * * * *